(12) United States Patent
Stoddard et al.

(10) Patent No.: US 10,893,884 B2
(45) Date of Patent: Jan. 19, 2021

(54) ULTRASONIC INSTRUMENTS FOR ROBOTIC SURGICAL SYSTEMS

(71) Applicant: Covidien LP, Mansfield, MA (US)

(72) Inventors: Robert Stoddard, Steamboat Springs, CO (US); Michael Lyons, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 217 days.

(21) Appl. No.: 16/081,780

(22) PCT Filed: Mar. 2, 2017

(86) PCT No.: PCT/US2017/020380
§ 371 (c)(1),
(2) Date: Aug. 31, 2018

(87) PCT Pub. No.: WO2017/151873
PCT Pub. Date: Sep. 8, 2017

(65) Prior Publication Data
US 2019/0029712 A1    Jan. 31, 2019

Related U.S. Application Data

(60) Provisional application No. 62/303,658, filed on Mar. 4, 2016.

(51) Int. Cl.
*A61B 17/32*     (2006.01)
*A61B 34/30*     (2016.01)
*A61B 17/00*     (2006.01)

(52) U.S. Cl.
CPC ...... *A61B 17/320092* (2013.01); *A61B 34/30* (2016.02); *A61B 2017/00477* (2013.01);
(Continued)

(58) Field of Classification Search
CPC ............ A61B 17/320092; A61B 34/30; A61B 2034/302; A61B 2017/320094;
(Continued)

(56) References Cited

U.S. PATENT DOCUMENTS 6,783,524 B2   8/2004  Anderson et al.
7,824,401 B2  11/2010  Manzo et al.
(Continued)

OTHER PUBLICATIONS

International Search Report dated Jun. 7, 2017, issued in PCT/US2017/020380.
(Continued)

*Primary Examiner* — Katrina M Stransky

(57) ABSTRACT

An ultrasonic surgical instrument including a housing, an ultrasonic generator, a waveguide assembly, and a retainer. The housing defines a cavity and is configured to mount to a linkage of a surgical robot. The ultrasonic generator includes a portion that is positioned within the cavity. The waveguide assembly is coupled to the ultrasonic generator and includes a portion that is positioned within the cavity. The retainer is positioned over the proximal connector and is engaged with the housing to secure the portions of the ultrasonic generator and the proximal connector within the cavity.

7 Claims, 9 Drawing Sheets

(52) U.S. Cl.
CPC ............... *A61B 2017/00734* (2013.01); *A61B 2017/320093* (2017.08); *A61B 2017/320094* (2017.08); *A61B 2034/302* (2016.02)

(58) Field of Classification Search
CPC ......... A61B 2017/320093; A61B 2017/00477; A61B 2017/00734
See application file for complete search history.

(56) References Cited

U.S. PATENT DOCUMENTS

| | | |
|---|---|---|
| 8,827,996 B2 | 9/2014 | Scott et al. |
| 8,828,023 B2 | 9/2014 | Neff et al. |
| 2002/0177843 A1 | 11/2002 | Anderson et al. |
| 2007/0239028 A1 | 10/2007 | Houser et al. |
| 2013/0144285 A1 | 6/2013 | Twomey et al. |
| 2014/0005681 A1 | 1/2014 | Gee et al. |
| 2014/0276931 A1* | 9/2014 | Parihar .................. A61B 34/37 606/130 |
| 2015/0265307 A1 | 9/2015 | Smith et al. |

OTHER PUBLICATIONS

European Search Report dated Sep. 16, 2019, issued in EP Appln. No. 17760783.
Chinese First Office Action dated Aug. 31, 2020 corresponding to counterpart Patent Application CN 201780014342.0.
European Office Action dated Jul. 17, 2020 corresponding to counterpart Patent Application EP 17760783.5.

* cited by examiner

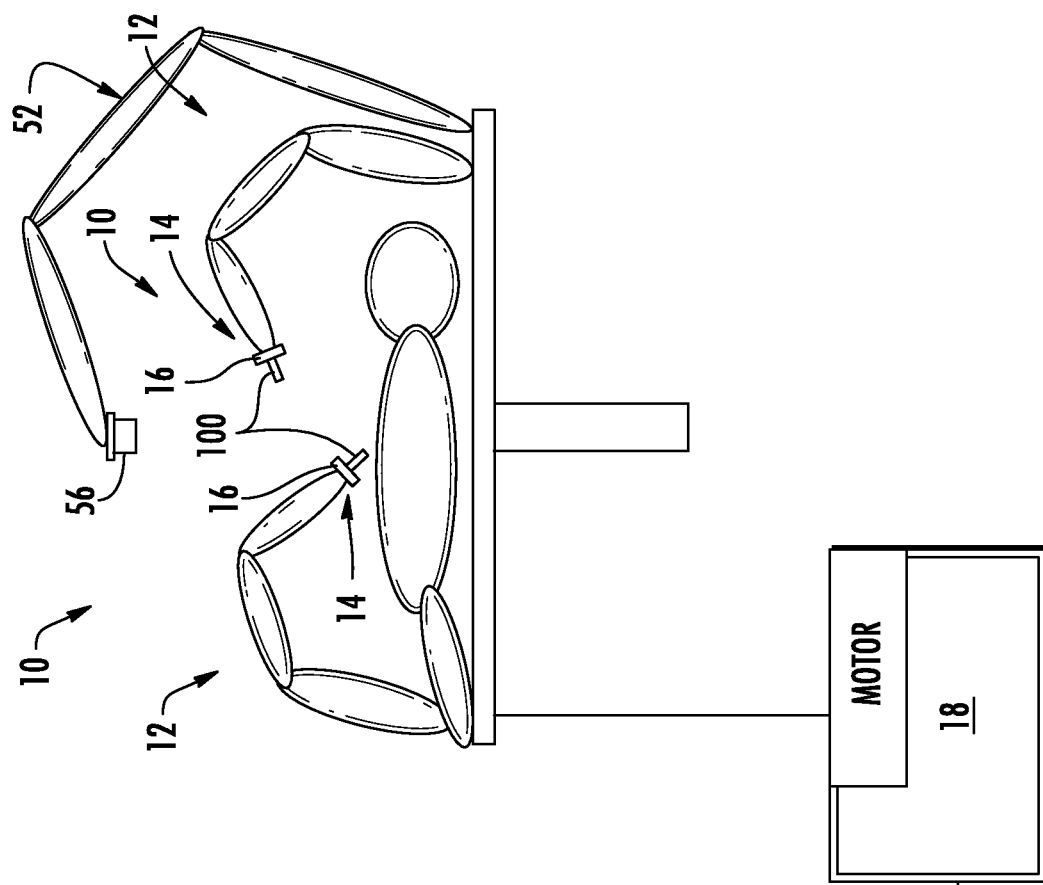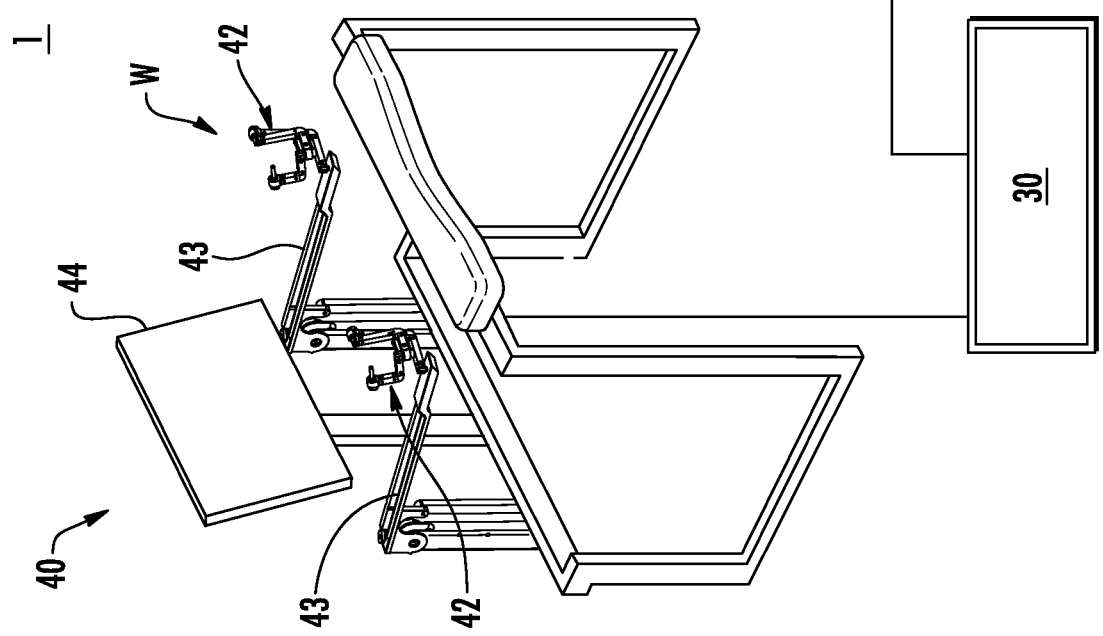

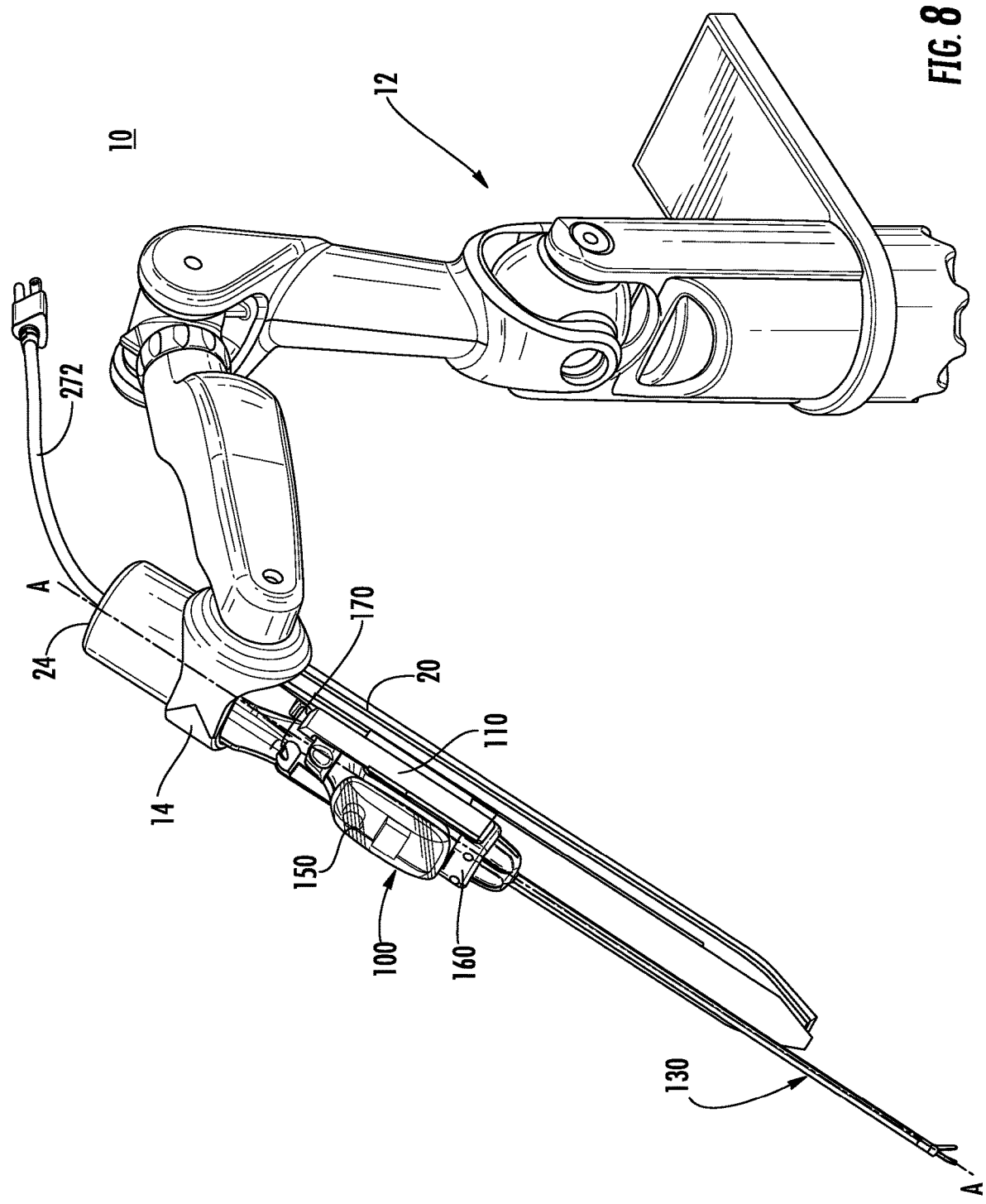

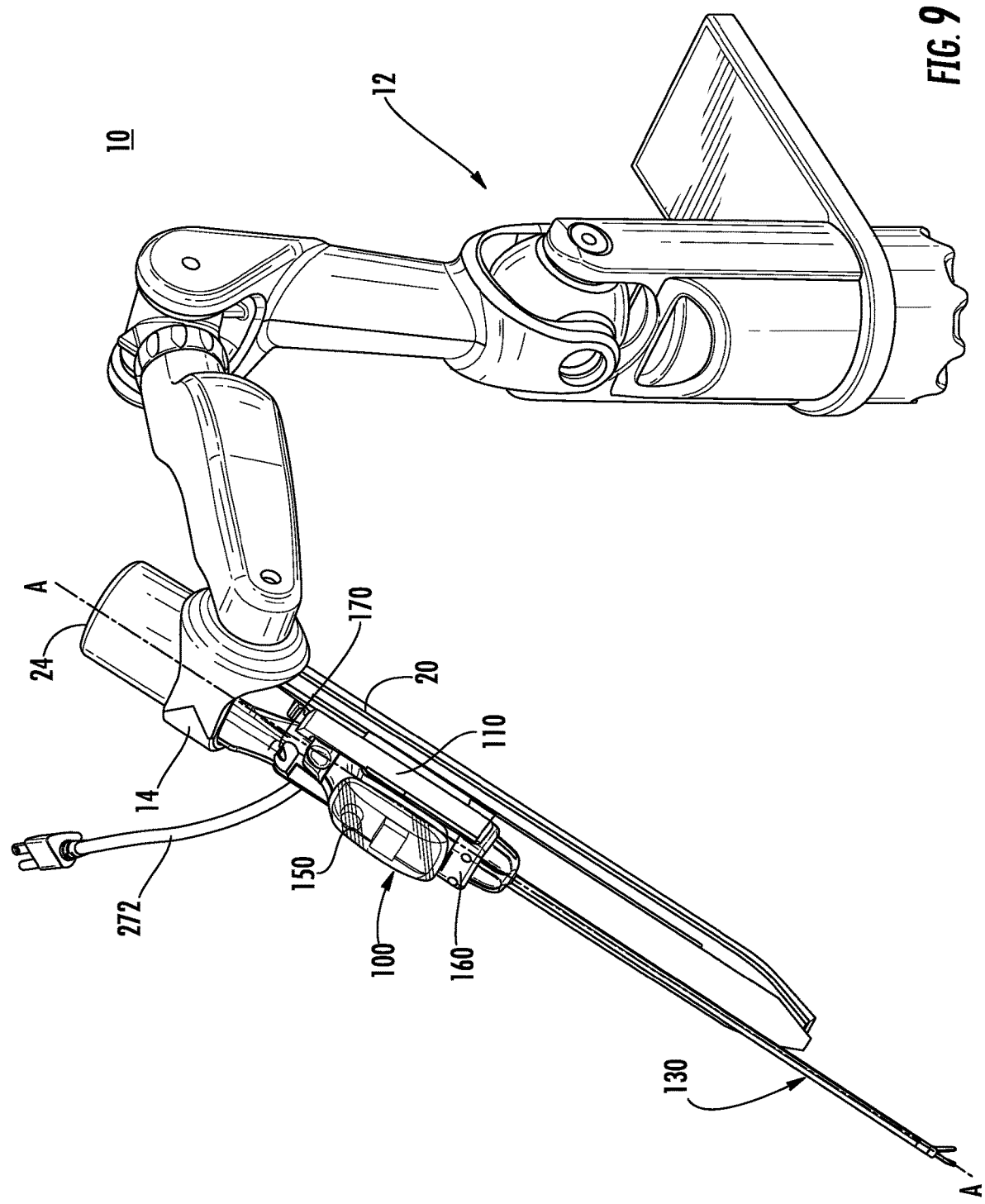

ULTRASONIC INSTRUMENTS FOR ROBOTIC SURGICAL SYSTEMS

CROSS-REFERENCE TO RELATED APPLICATIONS

This application is a U.S. National Stage Application filed under 35 U.S.C. § 371(a) of International Patent Application Serial No. PCT/US2017/020380, filed Mar. 2, 2017, which claims the benefit of and priority to U.S. Provisional Patent Application Ser. No. 62/303,658, filed Mar. 4, 2016, the entire disclosure of which is incorporated by reference herein.

BACKGROUND

1. Technical Field

The present disclosure relates to robotic surgical systems and, more specifically, to ultrasonic instruments for use with robotic surgical systems.

2. Discussion of Related Art

Robotic surgical systems such as teleoperative systems are used to perform minimally invasive surgical procedures. Minimally invasive surgical procedures offer many benefits over traditional open surgery techniques, including less pain, shorter hospital stays, quicker return to normal activities, minimal scarring, reduced recovery time, and less injury to tissue.

Robotic surgical systems can have a number of robotic arms that move attached instruments or tools, such as an image capturing device, a stapler, an electrosurgical instrument, an ultrasonic instrument, etc., in response to movement of input devices by a surgeon viewing images captured by the image capturing device of a surgical site. During a surgical procedure, each of the instruments is inserted through one or more natural openings or incisions made in the patient and advanced to a surgical site to manipulate tissue. The openings are placed about the patient's body so that the surgical instruments may be used to cooperatively perform the surgical procedure and the image capturing device may view the surgical site.

When an ultrasonic instrument is attached to a robotic arm, a source of ultrasonic energy is required to drive a waveguide of the ultrasonic instrument. This may require an ultrasonic generator to be connected to the ultrasonic instrument.

SUMMARY

This disclosure relates generally to robotic surgical systems that include an ultrasonic surgical instrument with an ultrasonic generator. The ultrasonic instrument may draw electrical energy through an instrument drive unit or from a linkage of a surgical robot with which the ultrasonic instrument is associated. Alternatively, the ultrasonic instrument may include a battery to supply the ultrasonic generator with electrical energy.

In an aspect of the present disclosure, an ultrasonic surgical instrument for use with a surgical robot includes a housing, an ultrasonic generator, and a waveguide assembly. The housing is configured to mount to a linkage of the surgical robot and defines a cavity. The ultrasonic generator is at least partially disposed within the cavity of the housing. The waveguide assembly is coupled to the ultrasonic generator and is at least partially disposed within the cavity of the housing.

In aspects, the surgical instrument includes a battery that is disposed within the cavity. The battery may be configured to supply the ultrasonic generator with electrical energy.

In some aspects, the waveguide assembly includes a proximal connector and a waveguide extending from the proximal connector. The surgical instrument may include a retainer that is positioned over the proximal connector and engaged with the housing to secure the ultrasonic generator and the proximal connector within the cavity. The retainer may include screws (or other fastening members) that are threadably (or otherwise) engaged with the housing to secure the retainer to the housing. The retainer may include contacts that electrically couple to complementary contacts of the ultrasonic generator to provide signal communication between the ultrasonic generator and the surgical robot.

In certain aspects, the waveguide assembly includes a proximal connector and a waveguide extending from the proximal connector. The waveguide may include a blade at a distal portion thereof. The waveguide assembly may also include an inner tube that is disposed over the waveguide and a clamping member pivotally supported at a distal portion of the inner tube. The blade may be rotatably fixed about the longitudinal axis relative to the housing. The ultrasonic generator may include a horn that is coupled to the waveguide. The horn may be configured to ultrasonically drive the waveguide.

In particular aspects, the surgical instrument may include a drive rod that is disposed within the housing which is configured to transition the clamping member between an open position, wherein the clamping member is spaced apart from the blade, and a clamped position, wherein the clamping member is approximated with the blade. The drive rod may include a distal engagement feature that is engaged with the proximal connector to transition the clamping member between the open and clamped positions in response to translation of the drive rod. Translation of the drive rod may translate an outer tube which engages the clamping member to transition the clamping member between the open and clamped positions. The surgical instrument may include a lead screw that is engaged with the drive rod and is configured to engage an instrument drive unit. The drive rod configured to translate within the housing in response to rotation of the lead screw.

In another aspect of the present disclosure, a surgical robot includes a linkage and an ultrasonic surgical instrument. The linkage has first and second end portions. The second end portion is movable relative to the first end portion and defines an instrument axis. The ultrasonic surgical instrument is mounted to the second end portion of the linkage and is translatable along the instrument axis. The ultrasonic surgical instrument includes a housing, an ultrasonic generator, and a waveguide assembly. The housing is mounted to the second end portion and defines a cavity. The ultrasonic generator is positioned within the cavity of the housing. The waveguide assembly is coupled to the ultrasonic generator and is positioned within the cavity.

In aspects, the ultrasonic surgical instrument is rotatable about the instrument axis. The second end portion may include a rail that is parallel to and rotatably about the instrument axis. The surgical robot may include an instrument drive unit that is slidably disposed on the rail and coupled to the housing.

In some aspects, the first end portion of the linkage is in electrical communication with the ultrasonic generator and is configured to provide electrical energy to the ultrasonic generator which is configured to convert the electrical energy to ultrasonically drive the waveguide. The first end portion of the linkage may be in electrical communication with the ultrasonic generator through the instrument drive unit.

In another aspect of the present disclosure, a method of assembly an ultrasonic surgical instrument includes coupling an ultrasonic generator to a waveguide assembly with a retainer disposed between the waveguide assembly and the ultrasonic generator, positioning a portion of the ultrasonic generator and a portion of the waveguide assembly within the housing, and engaging the housing with the retainer to secure the retainer, ultrasonic generator, and the waveguide assembly to the housing. When the ultrasonic generator is positioned within the housing, the ultrasonic generator is in electrical communication with an energy source via the housing.

In aspects, the method includes positioning a battery within the housing. The battery may be in electrical communication with ultrasonic generator via the housing to supply energy to the ultrasonic generator. Positioning the battery within the housing may occur before positioning a portion of the ultrasonic generator and the portion of the waveguide assembly within the housing.

Further, to the extent consistent, any of the aspects described herein may be used in conjunction with any or all of the other aspects described herein.

BRIEF DESCRIPTION OF THE DRAWINGS

Various aspects of the present disclosure are described herein below with reference to the drawings, which are incorporated in and constitute a part of this specification, wherein:

FIG. 1 is a schematic illustration of a user interface and a robotic system of a robotic surgical system in accordance with the present disclosure;

FIG. 8 is a perspective view of yet another arm of the robotic system of FIG. 1; and FIG. 9 is a perspective view of yet another arm of the robotic system of FIG. 1.

DETAILED DESCRIPTION

Figure 2:
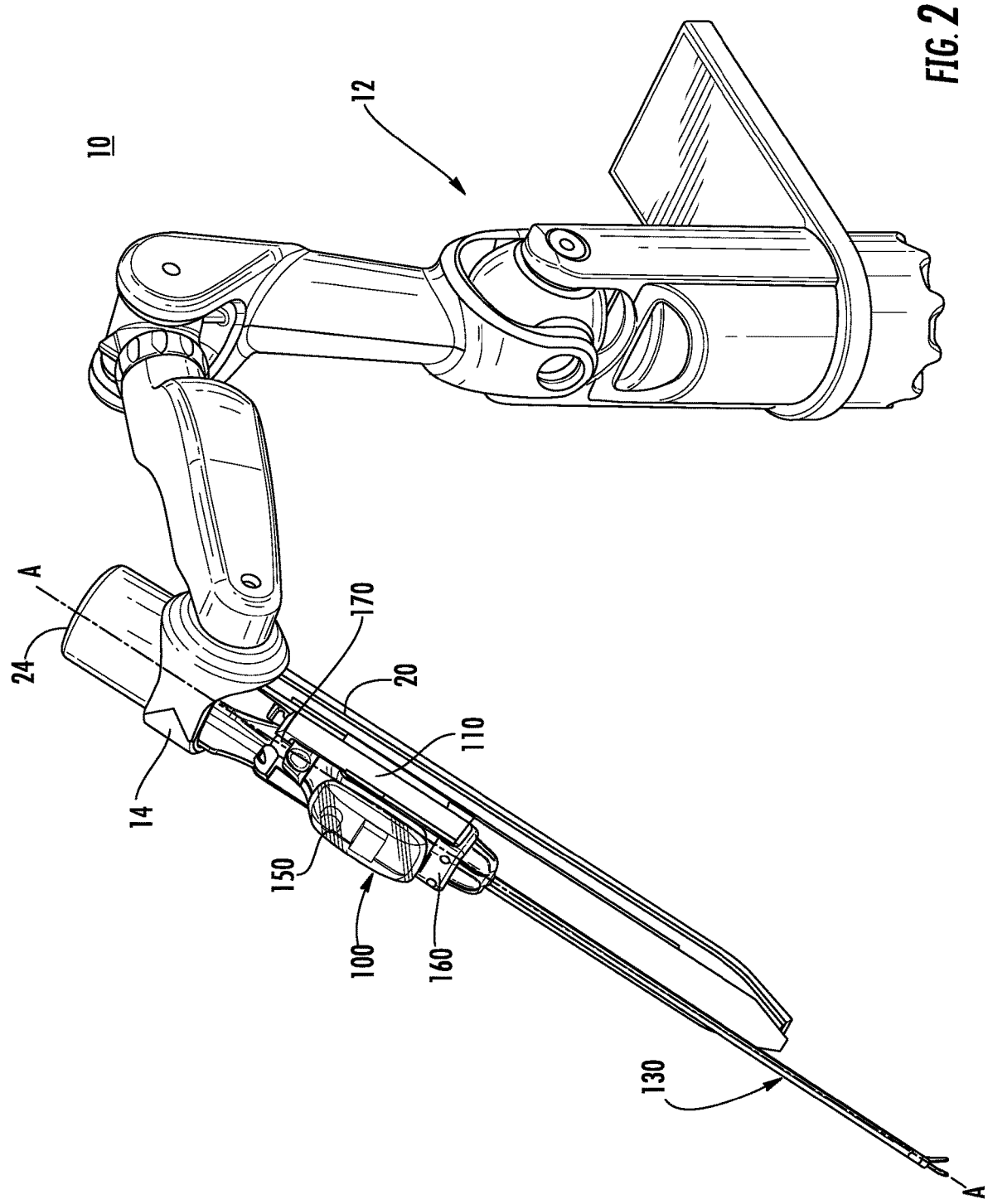
FIG. 2 is a perspective view of an arm of the robotic system of the robotic surgical system of FIG. 1 including a surgical instrument attached to a tool rail of the arm.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is farthest from the patient and the term "distal" refers to the portion of the device or component thereof that is closest to the patient.

This disclosure relates generally to an ultrasonic surgical instrument for use with a robotic system. The ultrasonic surgical instrument includes an ultrasonic generator and a waveguide assembly, each of which is at least partially disposed within the housing. The housing is configured to electrically couple the ultrasonic generator to a source of energy. The source of energy may be a battery disposed within the housing or within the linkage. Alternatively, the source of energy may be remote to the linkage and be in electrical communication with the housing through the linkage. Electrically coupling the ultrasonic generator to the source of energy through the housing may reduce peripheral attachments of the ultrasonic surgical instrument.

It is contemplated that the ultrasonic generator can be used with an ultrasonic surgical instrument for use with a robotic system and a handheld ultrasonic surgical system. Using the same ultrasonic generator for a robotic system and handheld system can reduce costs over requiring separate ultrasonic generators for each system.

Referring to FIG. 1, a robotic surgical system 1 in accordance with the present disclosure is shown generally as a robotic system 10, a processing unit 30, and a user interface 40. The robotic system 10 generally includes linkages or arms 12 and a robot base 18. The arms 12 moveably support and each has an end 14 that supports a tool or surgical instrument 100 which is configured to act on tissue. In addition, the ends 14 of the arms 12 may include an imaging device 16 for imaging a surgical site. The user interface 40 is in communication with robot base 18 through the processing unit 30.

The user interface 40 includes a display device 44 which is configured to display three-dimensional images. The display device 44 displays three-dimensional images of the surgical site which may include data captured by imaging devices 16 positioned on the ends 14 of the arms 12 and/or include data captured by imaging devices that are positioned about the surgical theater (for example, an imaging device positioned within the surgical site, an imaging device positioned adjacent the patient, or an imaging device 56 positioned at a distal end of an imaging linkage or arm 52). The imaging devices (for example, imaging devices 16, 56) may capture visual images, infra-red images, ultrasound images, X-ray images, thermal images, and/or any other known real-time images of the surgical site. The imaging devices transmit captured imaging data to the processing unit 30 which creates three-dimensional images of the surgical site in real-time from the imaging data and transmits the three-dimensional images to the display device 44 for display.

The user interface 40 also includes input handles 42 which are supported on control arms 43 which allow a clinician to manipulate the robotic system 10 (for example, move the arms 12, the ends 14 of the arms 12, and/or the surgical instruments 100). Each of the input handles 42 is in communication with the processing unit 30 to transmit control signals thereto and to receive feedback signals therefrom. Additionally or alternatively, each of the input handles 42 may include input devices (not shown) which allow the surgeon to manipulate (e.g., clamp, grasp, fire, open, close, rotate, thrust, slice, etc.) the surgical instruments 100 supported at the ends 14 of the arms 12.

For a detailed discussion of the construction and operation of a robotic surgical system 1, reference may be made to U.S. Pat. No. 8,828,023, the entire contents of which are incorporated herein by reference.

As noted briefly above, the arms 12 of the surgical robot 10 are configured to support surgical instruments 100. With reference to FIG. 2, a perspective view of an arm 12 of the surgical robot 10 where a tool rail 20 is shown supporting an ultrasonic instrument 100 in accordance with the present disclosure. The tool rail 20 includes an instrument drive unit (IDU) 24. The tool rail 20 defines a longitudinal axis A-A which passes through a center of the IDU 24. The end 14 of the arm 12 is configured to rotate the tool rail 20 and the IDU 24 about the longitudinal axis A-A. In addition, the IDU 24 and/or the ultrasonic instrument 100 are translatable along the tool rail 20, and thus along the longitudinal axis A-A.

Figure 3:
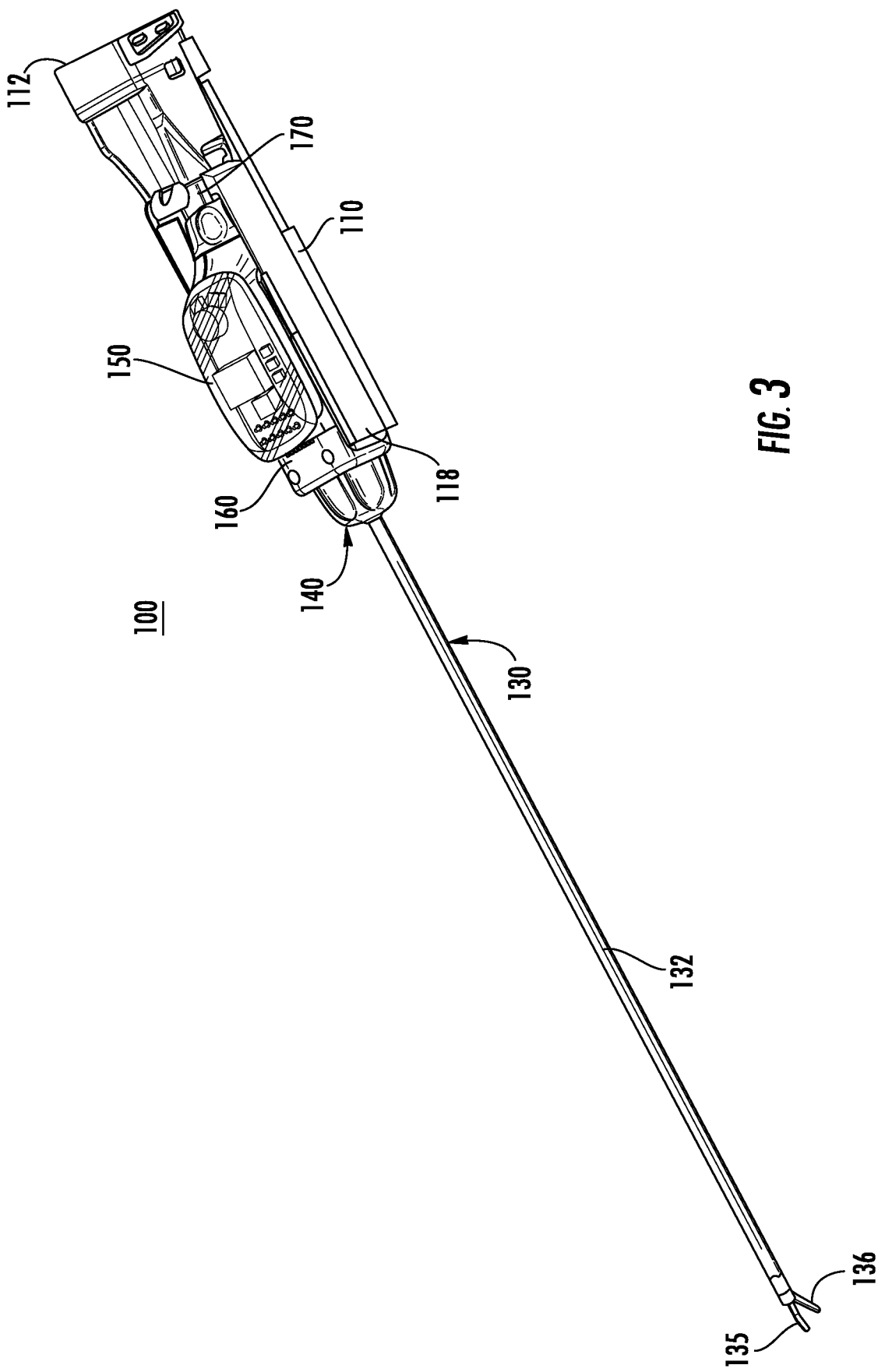
FIG. 3 is a perspective view of the surgical instrument of FIG. 2 detached from the tool rail of the arm.
Figure 4:
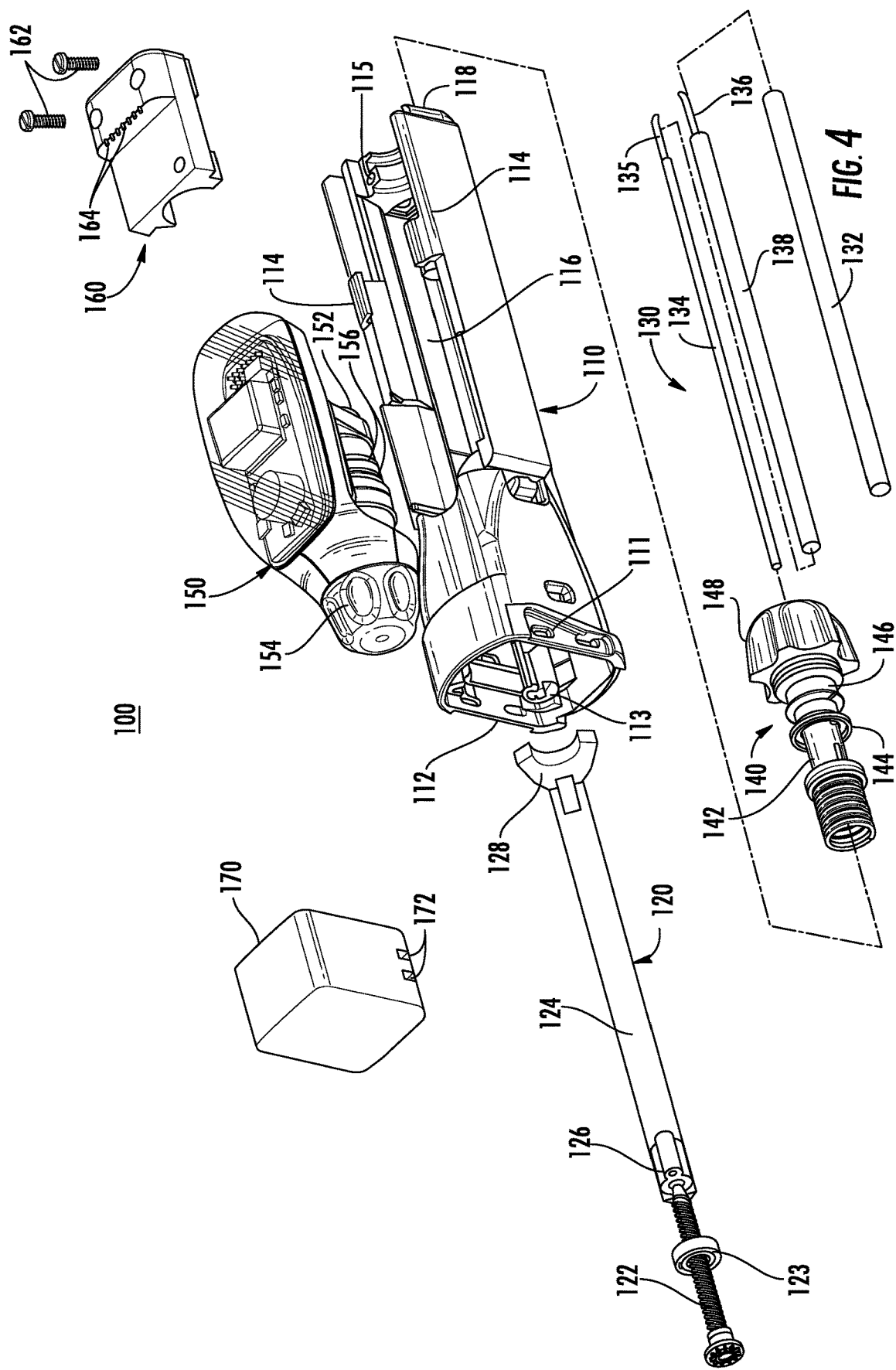
FIG. 4 is an exploded view, with parts separated, of the surgical instrument of FIG. 3.

With additional reference to FIGS. 3 and 4, the ultrasonic instrument 100 includes a housing 110, a waveguide assembly 130, an ultrasonic generator 150, and a retainer 160. The housing 110 includes sidewalls 114 defining a suitably-sized cavity 116 within which an actuation assembly 120, a proximal portion of the waveguide assembly 130, and a portion of the ultrasonic generator 150 are disposed. A proximal end 112 of the housing 110 is configured to detachably couple the ultrasonic instrument 100 to the IDU 24. For example, the proximal end 112 of the housing 110 includes openings 111 that align with corresponding mating interfaces (not shown) formed on a distal end of the IDU 24, which allow the ultrasonic instrument 100 to firmly attach to the arm 12.

The actuation assembly 120 is configured to actuate a clamping member 136 relative to a blade 135 of the waveguide assembly 130. In this regard, the actuation assembly 120 includes a lead screw 122 extending from a drive rod 124. The lead screw 122 is rotatably supported within a bearing 123, which is received and longitudinal fixed within a recess 113 defined in the proximal end 112 of the housing 110. The drive rod 124 includes a proximal engagement feature 126 that threadably engages the lead screw 122 such that when the ultrasonic instrument is mounted to the IDU 24, rotation of the lead screw 122 affects translation of the drive rod 124 parallel to the longitudinal axis A-A. The drive rod 124 also includes a distal engagement feature 128 that engages a portion of the waveguide assembly 130 as detailed below.

The waveguide assembly 130 delivers energy to the blade 135 for treating tissue and includes an outer tube 132, an inner tube 133, a waveguide 134, the clamping member 136, and a proximal connection assembly 140. The outer tube 132 is an elongate member that is disposed about the longitudinal axis A-A when the housing 110 is supported on the tool rail 20 (FIG. 2). The waveguide 134 is disposed within the inner tube 133 and includes the blade 135 extending from a distal end portion thereof. The clamping member 136 is pivotally supported at the distal portion of the inner tube 133, as described in further detail below, and is actuatable between an open position and a clamped position. In the open position, the clamping member 136 is spaced apart from the blade 135. In the clamped position, the clamping member 136 is approximated with the blade 135 to clamp tissue therebetween.

The proximal connection assembly 140 couples the waveguide assembly 130 to the housing 110 and includes a proximal connector 142, an approximation ring 144, a mounting ring 146, and a rotation ring 148. The proximal connector 142 is disposed within the cavity 116 of the housing and is associated with the waveguide 134. Specifically, the proximal connector 142 is engaged with the generator 150 to affect ultrasonic translation of the waveguide 134 within the outer tube 132. The approximation ring 144 is disposed about the proximal connector 142 and is engaged by the distal engagement feature 128 of the drive rod 124 to thereby allow the clamping member 136 to be transitioned between the open and clamped position in response to translation of the drive rod 124. It is envisioned that translation of the outer tube 132 may transition the clamping member 136 between the open and clamped positions. The mounting ring 146 is supported within the distal end 118 of the housing 110 to position the waveguide 134 along the longitudinal axis A-A when the housing is supported on the rail 22. The rotation ring 148 is distal of the distal end 118 of the housing 110 and is rotatable about the longitudinal axis A-A to rotate the outer tube 132, the waveguide 134, and the clamping member 136 about the longitudinal axis A-A. Alternatively, the rotation ring 148 may be rotatably fixed relative to the housing 110.

Referring to FIGS. 3-6, as noted briefly above, the generator 150 is disposed substantially within the cavity 116 of the housing 110 and converts electrical energy received through electrical contact rings 156 into mechanical ultrasonic energy. Specifically, the generator 150 includes a horn or output connector 152 (FIG. 4) that is configured to couple to the waveguide 134 to deliver the mechanical ultrasonic energy to the waveguide 134 to translate the waveguide 134 along the longitudinal axis A-A. A torque knob 154 included in a proximal end of the generator 150 is rotatable to secure or couple the waveguide 134 to the horn 152.

The retainer 160 is slidably engaged with the sidewalls 114 of the housing 110 over the cavity 116 to secure the proximal connection assembly 140 within the housing 110. The retainer 160 may include retention screws 162 (or any type of retaining/coupling feature or fastening member) corresponding to fastener openings 115 (one shown) in the sidewalls 114 that secure the retainer 160 to the housing 110. Additionally or alternatively, the retainer 160 may include an engagement feature (not shown) that selectively engages the housing 110 to secure the retainer 160 to the housing 110. The retainer 160 may also include contacts 164 that engage contacts 158 of the generator 150 to transmit signals and/or electrical energy along pathways included on the housing 110 to the generator 150.

Figure 6:
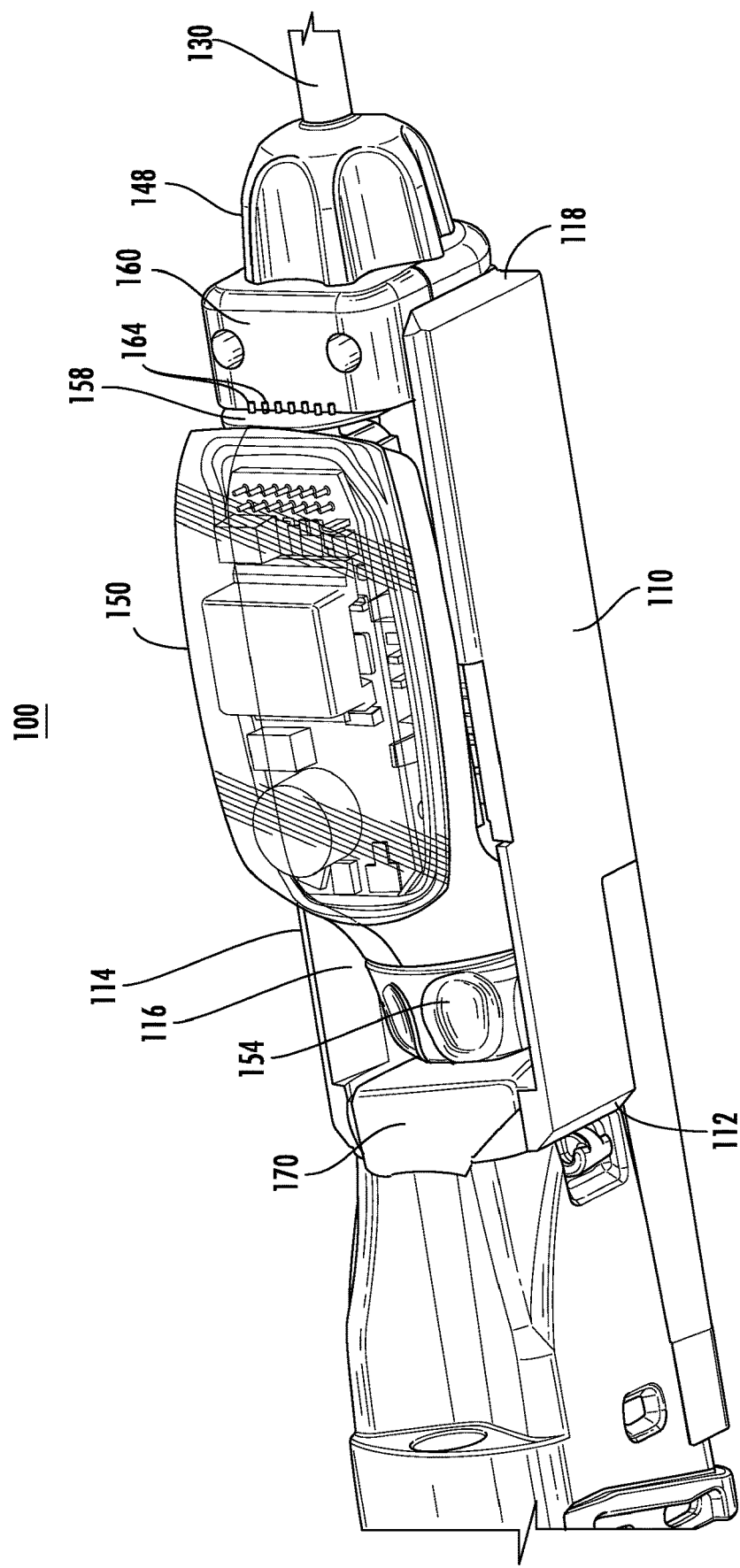
FIG. 6 is an enlarged perspective view of a portion of the surgical instrument of FIG. 3.

The ultrasonic instrument 100 can also include a battery 170 that provides electrical energy to the generator 150. As shown in FIG. 6, the battery 170 can be received within the cavity 116 proximal of the generator 150. The battery 170 can also engage the torque knob 154 to prevent rotation of the torque knob 154 when the generator 150 is received within the housing 116 as detailed below.

Figure 5:
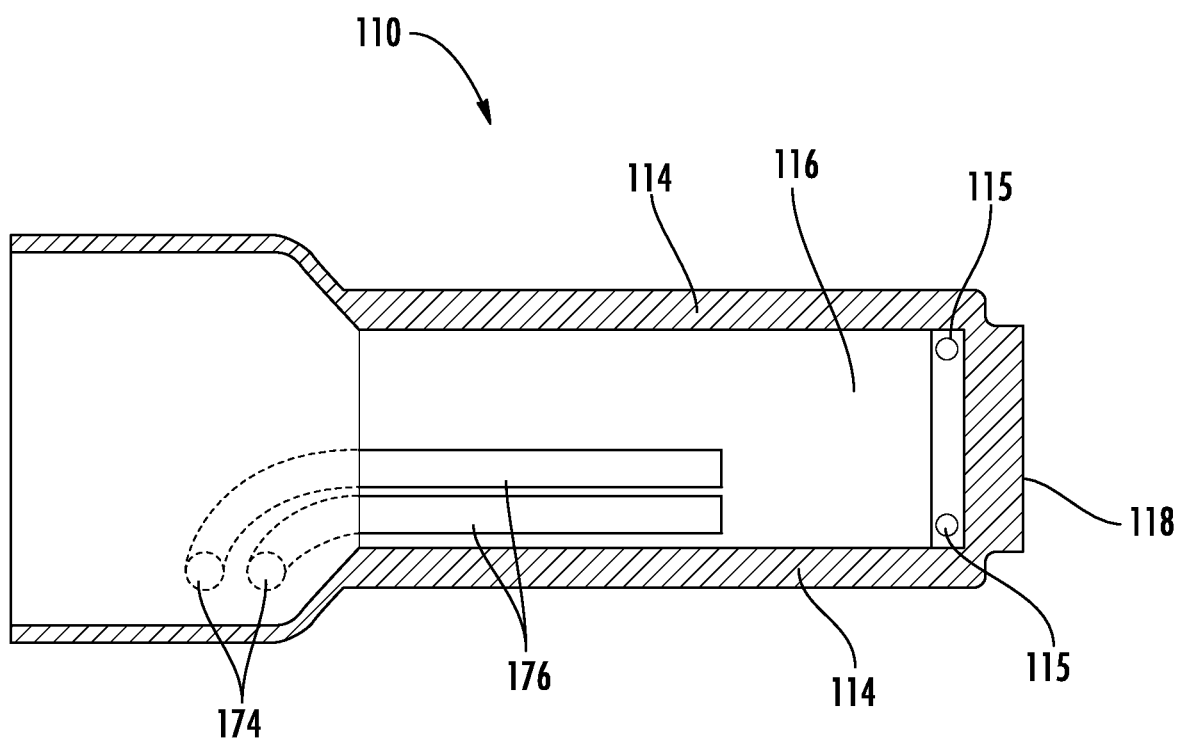
FIG. 5 is a top cross-sectional view of a housing of the surgical instrument of FIG. 3.

Referring to FIGS. 4 and 5, the battery 170 includes electrical contacts 172 (FIG. 4) that engage complementary contacts 174 within the cavity 116 of the housing 110. The housing 110 may include electrical traces 176 that electrically couple the electrical contacts 172 of the battery with the electrical contact rings 156 of the generator 150.

Referring to FIGS. 4 and 6, a method of assembling an ultrasonic instrument 100 is described in accordance with the present disclosure. Initially referring to FIG. 4, the retainer 160 is positioned over the proximal connection assembly 140 of the waveguide assembly 130. Next, the horn 152 of the generator 150 is threaded onto a proximal end portion of the waveguide assembly 130 with the retainer 160 disposed between the proximal connector 142 and a portion of the generator 150. When the proximal end portion of the waveguide assembly 130 is threaded into the horn 152, the torque knob 154 of the generator 150 is rotated to secure the waveguide assembly 130 to the horn 152. It is envisioned that as the torque knob 154 is rotated, the proximal connector 142 is drawn into the horn 152. As the proximal connector 142 is secured to the horn 152, the contacts 158 of the generator 150 may engage the contacts 164 of the retainer 160.

With the waveguide assembly 130 secured to the generator 150, the generator 150 and the proximal connection assembly 140 of the waveguide assembly 130 are positioned within the cavity 116 of the housing 110. As the proximal connection assembly 140 is positioned within the cavity 116, the mounting ring 146 of the proximal connection assembly 140 is received within a complementary structure defined by the distal end 118 of the housing 110 and the retainer 160 engages the sidewalls 114 of the housing 110. In addition, as the proximal connection assembly 140 is positioned in the cavity 116, the approximation ring 144 receives the distal engagement feature 128 of the drive rod 124. As shown in FIG. 6, when the generator 150 is positioned within the cavity 116, a portion of the generator 150 may be exposed above the sidewalls 114 of the housing 110 and the torque knob 154 is disposed within the cavity 116.

With the proximal connection assembly 140 and the generator 150 positioned within the cavity 116, the retainer 160 is engaged with the distal end 118 of the housing 110 to secure the proximal connection assembly 140 and the generator 150 within the cavity 116. Engaging the distal end 118 of the housing 110 with the retainer 160 can include inserting the screws 162 through the retainer 160 and into the distal end 118 of the housing 110 to secure the retainer 160 to the housing 110.

When the ultrasonic instrument 100 includes a battery 170, the battery 170 is positioned within the cavity 116 before the generator 150 is positioned within the cavity 116. As the generator 150 is positioned within the cavity 116, the torque knob 154 of the generator 150 can be received within a recess (not explicitly shown) of the battery 170. Alternatively, the battery 170 can be positioned over the torque knob 154 before the generator 150 is positioned in the cavity 116 such that the battery 170 and the generator 150 are positioned into the cavity 116 simultaneously.

When the ultrasonic instrument 100 is assembled, as detailed above, the ultrasonic instrument 100 can be mounted onto the tool rail 20 and coupled to the IDU 24. The ultrasonic instrument 100 can then be used in a robotic surgical procedure. Alternatively, the ultrasonic instrument 100 can be sterilized and sealed for use in during a future robotic surgical procedure. It is envisioned that the steps detailed above to assemble the ultrasonic instrument 100 may be performed in an order different from the order detailed above.

Figure 7:
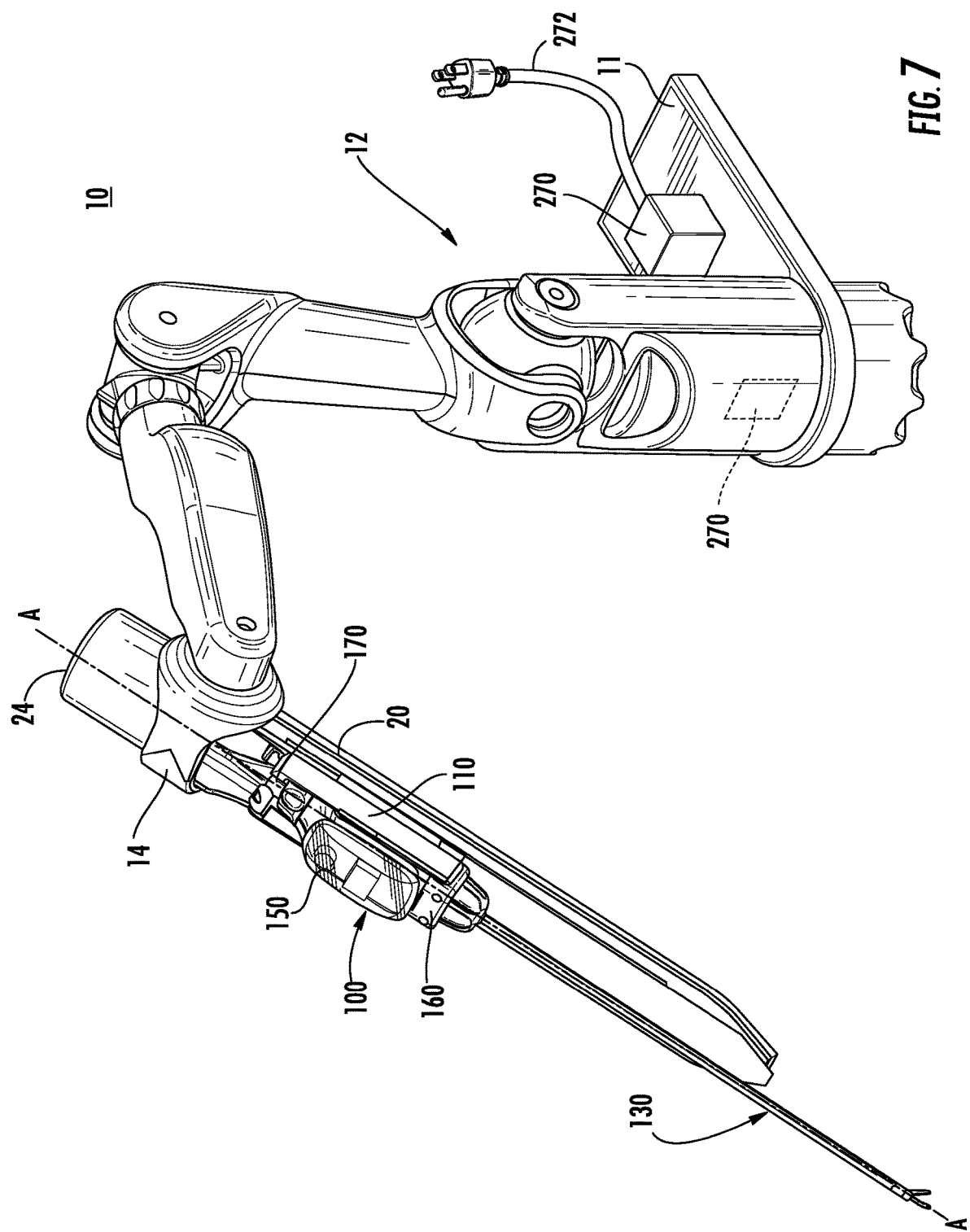
FIG. 7 is a perspective view of another arm of the robotic system of FIG. 1.

With reference to FIG. 7, the robotic system 10 may include an energy source 270 in electrical communication with the generator 150 to provide the generator with electrical energy. The energy source 270 can be positioned within a linkage 12 of the robotic system 10 or can be positioned on a base 11 supporting the linkages 12. For example, the energy source 270 can be positioned on a base 11 of the robotic system 10. The energy source 270 can include a battery and/or can be connected to an external source of energy, e.g., a wall socket, via a cord 272 that extends from the energy source 270.

The IDU 24 may be in electrical communication with the energy source 270 and may electrically couple to the traces 176 (FIG. 5) of the housing 110 to electrically couple the energy source 270 to the generator 150.

With reference to FIG. 8, the robotic system 10 may include a cord 272 that extends from the IDU 24 that is in electrical communication with the generator 150. The cord 272 is configured to plug into a source of electrical energy to provide electrical energy to the generator 150 through the IDU 24 as detailed above.

Referring to FIG. 9, the instrument 100 may include a cord 272 that extends from the housing 110 that is in communication with the traces 176 (FIG. 5) to provide electrical energy to the generator 150.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An ultrasonic surgical instrument for use with a surgical robot, the ultrasonic surgical instrument comprising:
    a housing configured to mount to a linkage of a surgical robot and defining a cavity;
    an ultrasonic generator at least partially disposed within the cavity of the housing;
    a waveguide assembly coupled to the ultrasonic generator and at least partially disposed within the cavity of the housing, the waveguide assembly including:
        a proximal connector and a waveguide extending from the proximal connector;
        a blade at a distal portion of the waveguide;
        an inner tube disposed over the waveguide; and
        a clamping member pivotally supported at a distal portion of the inner tube;
    a lead screw disposed within the housing, configured to engage an instrument drive unit;
    a drive rod disposed within the housing and configured to translate within the housing in response to rotation of the lead screw, the drive rod including:
        an engagement feature, configured to engage the lead screw; and
        a distal engagement feature engaged with the proximal connector to transition the clamping member, in response to translation of the drive rod, between an open position, wherein the clamping member is spaced apart from the blade, and a clamped position, wherein the clamping member is approximated with the blade.

2. The surgical instrument according to claim 1, further comprising a battery disposed within the cavity, the battery configured to supply the ultrasonic generator with electrical energy.

3. The surgical instrument according to claim 1, further comprising a retainer positioned over the proximal connector and engaged with the housing to secure the ultrasonic generator and the proximal connector within the cavity.

4. The surgical instrument according to claim 3, wherein the retainer includes fastening members engaged with the housing to secure the retainer to the housing.

5. The surgical instrument according to claim 3, wherein the retainer includes contacts that electrically couple to complementary contacts of the ultrasonic generator to provide signal communication between the ultrasonic generator and a surgical robot.

6. The surgical instrument according to claim 1, wherein the ultrasonic generator includes a horn coupled to the waveguide, the horn configured to ultrasonically drive the waveguide.

7. The surgical instrument according to claim 1, wherein translation of the drive rod translates an outer tube which engages the clamping member to transition the clamping member between the open and clamped positions.

* * * * *